US012629227B2

(12) United States Patent
Pruckner et al.

(10) Patent No.: US 12,629,227 B2
(45) Date of Patent: May 19, 2026

(54) CARRIER ELEMENT FOR SUPPORTING AT LEAST ONE MEDICAL OR DENTAL INSTRUMENT IN A CLEANING OR CARE DEVICE

(71) Applicant: W&H Dentalwerk Burmoos GmbH, Bürmoos (AT)

(72) Inventors: Christian Pruckner, Vienna (AT); Manfred Kainhofer, Wals-Siezenheim (AT); Michael Reiter, Elsbethen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 312 days.

(21) Appl. No.: 18/531,171

(22) Filed: Dec. 6, 2023

(65) Prior Publication Data
US 2024/0108431 A1 Apr. 4, 2024

Related U.S. Application Data

(62) Division of application No. 16/924,748, filed on Jul. 9, 2020, now abandoned.

(30) Foreign Application Priority Data

Jul. 11, 2019 (EP) .................................... 19185658

(51) Int. Cl.
A61B 50/33 (2016.01)
A61B 50/34 (2016.01)
(Continued)

(52) U.S. Cl.
CPC .............. *A61B 50/33* (2016.02); *A61B 50/34* (2016.02); *A61C 19/02* (2013.01); *A61L 2/26* (2013.01);
(Continued)

(58) Field of Classification Search
CPC ......... A61B 50/20; A61B 50/30; A61B 50/33; A61B 50/34; A61B 90/98; A61L 2/07;
(Continued)

(56) References Cited

U.S. PATENT DOCUMENTS

| | | | |
|---|---|---|---|
| 7,362,228 B2 * | 4/2008 | Nycz | A61F 2/4657 |
| | | | 340/568.1 |
| 8,020,768 B2 * | 9/2011 | Ramos-Elizondo | |
| | | | G06Q 10/087 |
| | | | 235/487 |

(Continued)

FOREIGN PATENT DOCUMENTS

| | | |
|---|---|---|
| JP | H11501838 A | 2/1999 |
| JP | 2006246372 A | 9/2006 |

(Continued)

OTHER PUBLICATIONS

Hirano, T., Chapter 4 Linear and Plate Antennas, *The Institute of Electronics, Information and Communication Engineers*, (url:http://ieice-hbkb.org/files/04/04gun_02hen_04.pdf) p. 3 and 11 of 15 (2013).

(Continued)

*Primary Examiner* — Luan K Bui
(74) *Attorney, Agent, or Firm* — Klarquist Sparkman, LLP

(57) ABSTRACT

A carrier element for supporting at least one medical or dental instrument in a cleaning or care device, wherein the instrument comprises a first transmitting and receiving unit for wireless transmission of electromagnetic radiation having data and/or energy with a second transmitting and receiving unit. A coupling antenna is provided on the carrier element, which receives and in turn emits the electromagnetic radiation wirelessly transmitted between the first and second transmitting and receiving units in order to support the wireless transmission of the electromagnetic radiation (Continued)

between the first transmitting and receiving unit and the second transmitting and receiving unit. A method for wireless transmission of electromagnetic radiation with a corresponding carrier element is also described.

20 Claims, 4 Drawing Sheets

(51) Int. Cl.

| | |
|---|---|
| *A61C 19/02* | (2006.01) |
| *A61L 2/26* | (2006.01) |
| *G06K 17/00* | (2006.01) |
| *A61B 90/98* | (2016.01) |
| *A61L 2/07* | (2006.01) |
| *A61L 103/15* | (2026.01) |

(52) U.S. Cl.
CPC .......... *G06K 17/0022* (2013.01); *A61B 90/98* (2016.02); *A61C 2204/005* (2013.01); *A61L 2/07* (2013.01); *A61L 2103/15* (2026.01)

(58) Field of Classification Search
CPC .. A61L 2/26; A61L 2202/24; A61L 2204/005; G06K 17/0022; A61C 19/02
USPC ............. 206/63.5, 363, 364, 368, 369, 438; 340/539.12, 572.1
See application file for complete search history.

(56) References Cited

U.S. PATENT DOCUMENTS

| | | | | |
|---|---|---|---|---|
| 2006/0043179 | A1* | 3/2006 | Nycz | A61B 50/33 |
| | | | | 235/385 |
| 2006/0244597 | A1* | 11/2006 | Tethrake | A61F 2/4657 |
| | | | | 340/572.1 |
| 2007/0160494 | A1* | 7/2007 | Sands | A61L 2/07 |
| | | | | 422/26 |
| 2008/0296373 | A1 | 12/2008 | Zmood et al. | |
| 2014/0110298 | A1* | 4/2014 | Khajavi | A61B 50/30 |
| | | | | 53/445 |
| 2014/0212833 | A1 | 7/2014 | Mangelberger et al. | |
| 2016/0022361 | A1 | 1/2016 | Khajavi | |
| 2018/0153639 | A1* | 6/2018 | Wehrle | G06K 19/0717 |
| 2020/0229887 | A1* | 7/2020 | Lento | A61L 2/07 |

FOREIGN PATENT DOCUMENTS

| | | |
|---|---|---|
| JP | 2006287317 A | 10/2006 |
| JP | 2010058811 A | 3/2010 |
| JP | 2016507259 | 3/2016 |
| JP | 2016518226 A | 6/2016 |
| WO | WO2019/012181 | 1/2019 |

OTHER PUBLICATIONS

Search Report for European U.S. Appl. No. 19/185,658, mailed Nov. 11, 2019.
Tanaka, S., Chapter 6 Aperture Antenna, *The Institute of Electronics, Information and Communication Engineers*, (url:http://ieice-hbkb.org/files/04/04gun_02hen_06.pdf) p. 3 of 16 (2013).

* cited by examiner

CARRIER ELEMENT FOR SUPPORTING AT LEAST ONE MEDICAL OR DENTAL INSTRUMENT IN A CLEANING OR CARE DEVICE

CROSS REFERENCE TO RELATED APPLICATION

The present application is a divisional of U.S. patent application Ser. No. 16/924,748, filed Jul. 9, 2020, which claims priority from pending European Patent Application No. 19185658.2, filed Jul. 11, 2019, which application are incorporated herein by reference.

FIELD

The present application relates to a carrier element for supporting at least one medical or dental instrument in a cleaning or care device and a method for the wireless transmission of electromagnetic radiation comprising data and/or energy through such a carrier element.

DESCRIPTION OF PRIOR ART

A coupling device for the wireless transmission of data and/or energy between a medical, in particular dental, instrument and a coupling part which can be connected thereto is known from the published application US 2014/0212833 A1. This coupling part can also be arranged inside a cleaning or care device, for example in a chamber, so that data and/or energy can be transmitted wirelessly between a medical, in particular dental, instrument and the cleaning or care device.

The transmission of data and/or energy at a cleaning or care device, in particular within the cleaning or care device or out of the cleaning or care device, is challenging, inter alia, due to metallic components of the cleaning or care device or electromagnetic fields existing during operation. This causes problems such as a reduced transmission range or interference and disturbing of the transmission of data and/or energy.

The solution known from the above-mentioned application US'833 A1 avoids these problems by placing the transmitting and receiving units of the instrument and the cleaning or care device on the respective couplings so that the two transmitting and receiving units are positioned as close to each other as possible. This solution works well in principle, but it limits the number of instruments that can be cleaned or cared for or maintained and with which data and/or energy can be exchanged to the number of existing coupling parts of the cleaning or care device.

SUMMARY

It is thus an object to create a more secure data and/or energy transmission for medical, in particular dental, instruments to be cleaned or cared for which are located close to or in a cleaning or care device. The data and/or energy transmission should be reliable and safe, especially without connecting the medical, in particular dental, instrument to a coupling part of the cleaning or care device.

The carrier element is configured to support or hold at least one medical or dental instrument in a cleaning or care device in order to clean or care for the at least one medical or dental instrument in the cleaning or care device. A first transmitting and receiving unit is arranged on the medical or dental instrument, which is configured for wireless transmission of electromagnetic radiation comprising data and/or energy with a second transmitting and receiving unit. At least one coupling antenna is provided on the carrier element, which is configured to receive the electromagnetic radiation transmitted wirelessly between the first transmitting and receiving unit and the second transmitting and receiving unit and to emit it again in order to support the wireless transmission of the electromagnetic radiation comprising data and/or energy between the first transmitting and receiving unit and the second transmitting and receiving unit.

Unless otherwise stated, it applies to all embodiments described that the wireless transmission of electromagnetic radiation comprising data and/or energy between the first transmitting and receiving unit and the second transmitting and receiving unit comprises a transmission in the direction of the first transmitting and receiving unit and/or in the direction of the second transmitting and receiving unit. The first and second transmitting and receiving units are preferably configured for data and/or energy transmission in the UHF and/or SHF frequency range. The first transmitter and receiver unit of the medical or dental instrument comprises, for example, an RFID label. The second transmitting and receiving unit comprises, for example, a reader for reading the first transmitting and receiving unit.

The provision of at least one coupling antenna on the carrier element improves and supports in a beneficial manner the data and/or energy transmission between the first transmitting and receiving unit and the second transmitting and receiving unit, preferably inside a cleaning or care device or when inserting the carrier element into the cleaning or care device or when removing the carrier element from the cleaning or care device, so that it is in particular no longer necessary to connect a medical, in particular dental, instrument to a coupling part of the cleaning or care device for the data and/or energy transmission.

The at least one coupling antenna is configured and intended in particular to counteract or reduce the negative effect of the metallic components of the cleaning or care device and of the electromagnetic fields as mentioned above on the transmission of electromagnetic radiation. The at least one coupling antenna is particularly preferably intended to couple or connect the first transmitting and receiving unit and the second transmitting and receiving unit communicatively with each other.

The support and/or improvement of the wireless transmission of electromagnetic radiation comprising data and/or energy by the at least one coupling antenna comprises for example affecting or changing the direction of emission of the electromagnetic radiation comprising data and/or energy, in particular in the direction of the first transmitting and receiving unit and/or the second transmitting and receiving unit;

an increase in the energy density of the electromagnetic radiation comprising data and/or energy;

a concentration or focusing of the electromagnetic radiation comprising data and/or energy;

an increase in the transmission range of the electromagnetic radiation comprising data and/or energy, in particular due to the affecting or changing of the direction of emission, increase in the energy density and/or concentration or focusing as mentioned above;

a reduction in the loss of the transmitted electromagnetic radiation, in particular of the data and/or energy, in particular due to the affecting or changing of the direction of emission, increase in the energy density and/or concentration or focusing as mentioned above.

The carrier element comprises, for example, a carrier plate, tray, basket or cassette or is configured as one of these elements.

The carrier plate is configured in particular as a plate or grid plate without side walls and without cover or lid. Preferably, the carrier plate is configured as an essentially flat surface. Preferably, the outer periphery of the carrier plate is formed by a frame with a plurality of sides arranged at an angle to each other. Preferably, the frame surrounds the plate or grid, which has a large number of openings or grid openings. Preferably the openings or grid openings are intended as a passage for a cleaning or care medium. Preferably, the frame does not comprise any openings or grid openings. Preferably, the at least one coupling antenna is provided on or in the carrier plate, in particular the grid plate and/or the frame.

The tray or basket comprises in particular a base plate or a bottom and a plurality of side walls connected to it and surrounding the base plate or bottom. Preferably, the base plate and/or the side walls comprise(s) a plurality of openings. Preferably, the tray or basket is configured as a screen or mesh basket with a large number of sieve openings. Preferably, the openings or sieve openings are intended as a passage for a cleaning or care medium. Preferably, at least one coupling antenna is provided on or in the base plate or the bottom and/or on or in at least one of the side walls.

The cassette comprises in particular a base or bottom, a plurality of side walls connected to it and surrounding the base, and a lid or cover. Preferably, the lid or cover is configured to be movable relative to the base and/or the side walls, e.g., pivotable, or removable therefrom. Preferably the lid or cover covers a plurality of side walls. Preferably the bottom, the side walls and the lid or cover delimit an interior of the cassette from the environment. Preferably, the bottom and/or the side walls and/or the lid or cover are provided with a large number of openings, for example elongated openings, which serve in particular as a passage for a cleaning or care medium. Preferably, the at least one coupling antenna is provided on or in the bottom and/or on or in at least one of the side walls and/or on or in the lid or cover.

The carrier element is configured in particular to be accommodated in a cleaning or care device. The carrier element is configured, for example, to be placed on the inside of a base or bottom of the cleaning or care device or to be inserted into a chamber of the cleaning or care device. The carrier element is preferably configured to be supported or detachably fastened to one or more holding elements of the cleaning or care device. The holding element comprises, for example, a guide rail or ridge or a projection through which the carrier element, in particular a bearing element of the carrier element matching or complementary to or connectable with the holding element, can be supported or fastened. The holding element of the cleaning or care device is provided in particular on the inside of the chamber. The bearing element of the carrier element is provided in particular on its bottom and/or on at least one of the side walls.

The carrier element is preferably at least partially made of metal and/or plastic and/or glass and/or ceramic. The metal comprises for example steel or a steel alloy. The selection of the material of the carrier element, in particular that part of the carrier element on which the at least one coupling antenna is provided or arranged, is preferably dependent on the type of coupling antenna. Thus, it is particularly advantageous for the function of a coupling antenna configured as a flat top antenna, in particular as a slot antenna, if it is surrounded by a metallic component of the carrier element.

The metallic component can, for example, be a metallic frame surrounding the slot or slot antenna or a metallic coating of a part of the carrier element surrounding the slot, for example of a part of the bottom, at least one side wall or the cover. The metallic component may also comprise a metallic part of the carrier element surrounding the slot, for example at least a metallic part of the bottom, at least one side wall or the cover. For the function of a coupling antenna configured as a metallic, (geometrically) linear antenna, for example as a rod antenna, it is advantageous if it is surrounded by an electrically non-conductive material, for example glass or plastic. Accordingly, preferably a section of the carrier element, for example a part of the floor, at least one side wall or cover, on or in which the (geometrically) linear antenna is located, is formed from an electrically non-conductive material.

Preferably the first transmitting and receiving unit or transponder unit, in particular the RFID label, arranged on the medical or dental instrument comprises an antenna, in particular an oscillating circuit, for receiving and/or transmitting the electromagnetic radiation comprising data and/or energy. Furthermore, the first transmitting and receiving unit comprises in particular a capacitor and/or a memory element, which are operatively connected to the antenna. The memory element stores in particular data for identifying the instrument, for example an identification code (uniquely) assignable to the instrument to which the first transmitting and receiving unit is attached, or codes for identifying the instrument via an external database, for example according to GS1 or HIBC standard.

Preferably, the first transmitter/receiver unit is configured as a passive first transmitter/receiver unit, which receives energy required in particular for communication and internal processes exclusively from the electromagnetic radiation emitted by the second transmitter/receiver unit. Particularly preferred, the first transmitter and receiver unit comprises one or more RFID labels.

The second transmitting and receiving unit, which is arranged remotely from the first transmitting and receiving unit, comprises in particular a reading device for reading and/or receiving the instrument-specific data stored in the memory element of the first transmitting and receiving unit, in particular the identification code. Preferably, the second transmitting and receiving unit in turn comprises an antenna, in particular a resonant circuit, for receiving and/or transmitting the electromagnetic radiation, a source for the electromagnetic radiation, for example a high-frequency module, and a controller. Preferably, the second transmitting and receiving unit also comprises an interface to a processing unit for further processing of the received data. The electromagnetic radiation emitted by the second transmitting and receiving unit provides energy for operation to the first transmitting and receiving unit. The second transmitting and receiving unit is either attached to or in the cleaning or care unit or is physically separated from it.

If the first and second transmitter and receiver units are connected to each other communicatively, i.e., if the first transmitting and receiving unit is located in the reading range of the second transmitting and receiving unit or in an electromagnetic field emitted by the second transmitting and receiving unit, in particular if the medical or dental instrument is or is being accommodated in the cleaning or care device, for example in a chamber of the cleaning or care device, the second transmitting and receiving unit is configured to determine or recognize the instrument-specific data, in particular the identification code, by wireless transmission of the electromagnetic radiation comprising data and/or energy. Preferably, the instrument-specific data determined in this way is forwarded to a processing unit, for example a processor or microcontroller, which is communicatively connected to the second transmitting and receiving unit. Preferably, the processing unit is configured to store and/or process these forwarded instrument-specific data in order to prove in particular that the medical or dental instrument whose instrument-specific data, in particular its identification code, has been received and forwarded has been accommodated and/or cleaned or cared for in the cleaning or care device.

The medical or dental instrument on which the first transmitter and receiver unit is mounted comprises for example: an instrument for medical or dental diagnosis; an instrument for medical or dental treatment; an instrument for delivering a medium and/or energy to a diagnosis or treatment site; an instrument for rotating or oscillating or vibrating drive of a tool; a drive device, for example a motor; an adapter; a coupling device; a connector; an active instrument requiring the supply of power from a power source for operation; a passive instrument without supply of power, for example a scraper, tweezers or scissors; a handpiece, handle element or contra-angle handpiece; a tool, for example a drill, blade, saw blade, scaler tip, shaver, nozzle, light or laser emitting tip, and similar tools.

Preferably at least one mechanical positioning element, for example a holder, is provided on the carrier element in order to position, in particular fix, the at least one medical or dental instrument on the carrier element. The positioning element is particularly preferably configured in such a way that the medical or dental instrument is disposed in a (pre)determined position, orientation and/or arrangement with respect to the carrier element and/or the at least one coupling antenna, so that the first transmitting and receiving unit faces the at least one coupling antenna and/or extends in the direction of the at least one coupling antenna. For example, the positioning element or holder is dimensioned or shaped such that only a certain portion of the medical or dental instrument can be accommodated therein, thereby assuming the predetermined position, arrangement or orientation. Alternatively or additionally, at least one mechanical engagement element is provided on each of the medical or dental instrument and the positioning element so that when the engagement elements engage or lock, the predetermined position, arrangement or orientation is assumed. Such positioning elements advantageously improve wireless communication, in particular the transmission of electromagnetic radiation, between the first transmitting and receiving unit and the at least one coupling antenna.

Preferably the at least one positioning element has a plug-in element with a receptacle into which the medical or dental instrument to be cleaned or cared for can be inserted. Alternatively or additionally the at least one positioning element comprises a clamping element or the plug-in receptacle is configured as a clamping element into which the medical or dental instrument to be cleaned or cared for can be clamped. Preferably, the plug-in receptacle or the clamping element defines an accommodation space in which at least a part of the medical or dental instrument can be accommodated, in particular clamped. Preferably, a wall defining the accommodation space is curved or shaped like an arc. Particularly preferred the accommodation space or the wall delimiting it is dimensioned or shaped in such a way or comprises one of the engagement elements in order to position the medical or dental instrument in the (pre)determined position as described above. Preferably the receptacle or clamping element comprises two spring arms or two bearing arms between which the plug-in receptacle is provided. The two spring arms or bearing arms preferably originate from a common base. The two spring arms or bearing arms are preferably bent. The two spring arms or bearing arms preferably each have a free end.

Preferably, the at least one positioning element is configured in one piece with the carrier element, for example on the bottom, on the base or grid plate and/or on one of the side walls. Alternatively, the at least one positioning element is detachably attached to the carrier element. Preferably a plurality of small openings, for example substantially circular openings, are provided on the carrier element for this purpose, into which a connecting element, for example an extension, of the at least one positioning element can be inserted in order to fasten the at least one positioning element to the carrier element. If the carrier element has a grid or grid plate as described above, it is also possible to fasten the at least one positioning element to the grid or grid plate, in particular by inserting the extension of the carrier element into one or more grid openings.

The at least one coupling antenna is preferably formed as part of the carrier element, in particular it is non-detachably connected to the carrier element and/or is formed integrally or in one-piece with the carrier element, in particular as a flat top or slot antenna. Alternatively, it is also possible to configure the at least one coupling antenna as a separate component which is inserted into the carrier element and/or connected to the carrier element and in particular can also be removed from it again. Thus, a retrofitting of a carrier element can be realized in an advantageous way. Preferably a holding body is provided, for example a plate, on or in which the at least one coupling antenna is provided, for example in the form of a slot in the holding body to form a slot antenna, or a holding body on or in which a (geometrically) linear antenna is formed, for example in the form of a rod or wire antenna, as described below.

Preferably, the at least one coupling antenna is configured as a (geometrically) linear antenna whose electrical conductor comprises in particular a metallic wire or a metallic rod. The (geometrically) linear antenna is configured in particular as a rod antenna or as a wire antenna or as a dipole antenna. By designing the coupling antenna as a linear antenna it is advantageously possible to select the dimension, in particular the length of the antenna independently of the dimensions of the carrier element, in particular it is possible that the length of the antenna is greater than the longest dimension or the longest outer side of the carrier element.

Preferably, the (geometrically) linear antenna is located in a recess of the carrier element, in particular in an opening in an outer wall of the carrier element, for example the bottom or base plate, a side wall or the cover. Thus, the linear antenna is advantageously integrated into the carrier element, in particular into its body, thus simplifying the handling of the carrier element. To achieve even better integration, the recess in which the linear antenna is located is preferably filled with an electrically non-conductive filling material, for example plastic or glass or ceramic. Preferably, the linear antenna is surrounded by an electrically non-conductive material, for example plastic or glass or ceramic, to form an antenna envelope which is accommodated in the recess of the carrier element. This reduces the risk of small instruments to be cleaned or maintained falling through the recess and being lost.

Preferably, the at least one coupling antenna is configured as a flat top antenna, preferably as a flat top antenna with an opening or aperture in an outer wall of the carrier element.

The flat top antenna is preferably configured as an antenna formed by a slot or slot antenna. A flat top antenna allows in an advantageous way a very simple production of the coupling antenna, for example by forming an opening, a breakthrough or a slot in a part of the carrier element.

Preferably the flat top antenna has an elongated slot or opening, for example straight or curved or rectangular or spiral. The different shapes allow the direction and/or shape and/or intensity of the emitted electromagnetic radiation to be varied in an advantageous way. Preferably, the slot or opening is provided in an outer wall of the carrier element, for example the bottom or base plate, a side wall or the cover.

Preferably the slot or aperture is filled with an electrically non-conductive material, for example plastic or glass or ceramic, in order to form in particular a continuous carrier element body. This reduces the risk of small instruments to be cleaned or cared for falling through the slot and getting lost.

Preferably, the length of the coupling antenna, in particular the slot, breakthrough or opening, is matched to the wavelength or frequency of the electromagnetic radiation comprising data and/or energy to be transmitted, in particular to electromagnetic radiation in the UHF and/or SHF frequency or wavelength range, preferably to electromagnetic radiation with a wavelength of about 25 cm-40 cm, preferably 29 cm-35 cm, and particularly preferably to a wavelength of about 34.6 cm or about 33 cm. Preferably, the slot or aperture has a length of half or quarter of the length of at least one wavelength to be transmitted, in particular the wavelength(s) mentioned above, thus ensuring in an advantageous way a reliable transmission of the electromagnetic radiation comprising data and/or energy. For example, a length of the slot or aperture is at least about 6.25 cm, preferably at least about 7.5 cm, preferably about 8.25 cm or about 8.65 cm or about 16.5 cm or about 17.3 cm. Preferably the slot has an elongated shape with at least one long side and one narrow side.

Preferably, the opening or the breakthrough or slot of the flat top antenna is larger, in particular considerably larger than the grid openings or (circular) openings for fixing the at least one positioning element or the at least one holder or the openings or elongated openings of the carrier element serving in particular as a passage for a cleaning or care product. Particularly preferably, these grid openings or (elongated) openings do not act as a coupling antenna for the electromagnetic radiation comprising data and/or energy and transmitted between the first and second transmitting and receiving unit, in particular for the radiation with SHF and/or UHF frequency or wavelength. Particularly preferably, the dimensions of these grid openings or (elongated) openings are dimensioned in such a way that they do not act as coupling antennas for the wavelengths or frequencies of the electromagnetic radiation comprising data and/or energy and transmitted between the first and second transmitting and receiving units, the wavelength of the electromagnetic radiation being particularly in the ranges described above. In this way, an undesirable influence of the grid openings or (elongated) openings on the transmission of the electromagnetic radiation between the first and second transmitting and receiving units is at least reduced or avoided in an advantageous manner.

In particular, the number of openings or breakthroughs or slots of the flat top antenna is considerably smaller than the number of grid openings or (circular) openings for fixing the at least one positioning element or the (elongated) openings of the carrier element serving in particular as a passage for a cleaning or care product. Preferably, the number of grid openings or (circular or elongated) openings is at least five times, preferably at least ten times greater than the number of flat top antennas or the openings or breakthroughs or slots of the flat top antenna. Preferably the flat top antennas or the openings or breakthroughs or slots of the flat top antenna are surrounded by a plurality of grid openings or (circular or elongated) openings of the carrier element.

Preferably, a plurality of coupling antennas is provided on a carrier element. This advantageously further improves the transmission of electromagnetic radiation comprising data and/or energy, as described in detail below according to various possible variants.

Preferably the a plurality of coupling antennas are provided on different sections or walls, for example on the bottom or on the base or grid plate and/or on one of the side walls and/or on the cover. This improves the transmission of electromagnetic radiation comprising data and/or energy, for example when a plurality of medical or dental instruments to be cleaned or cared for are arranged on the carrier element, with the first transmitting and receiving units pointing in different directions.

Alternatively or additionally two of the plurality of coupling antennas are arranged one inside the other. For example, at least one of the plurality of coupling antennas comprises a flat top antenna having an elongated slot in an outer wall of the metallic carrier element and another of the plurality of coupling antennas comprises a (geometrically) linear antenna, the linear antenna being disposed in the elongated slot of the flat top antenna. In particular, the opening or slot of the flat top antenna is filled with a filling material, in particular an electrically non-conductive filling material, in which the linear antenna is received or embedded. In addition to the improved transmission of the electromagnetic radiation, this arrangement results in a compact, space-saving arrangement of the a plurality of coupling antennas in an advantageous way.

Alternatively or additionally at least two of the plurality of coupling antennas are configured for the transmission of electromagnetic radiation of different frequencies. In particular, these coupling antennas for the transmission of different frequencies have different dimensions, especially different lengths. This is an advantageous way of creating a carrier element which can be sold and used in various countries in which different frequencies are used for data and/or energy transmission. The manufacturer of such a carrier element thus saves the need to produce different carrier elements for different countries.

Preferably a, in particular medical or dental cleaning or care device is provided for at least one medical or dental instrument, which comprises a carrier element described above and a second transmitting and receiving unit.

The cleaning or care device preferably comprises a housing, the second transmitting and receiving unit being arranged in the housing or outside the housing.

The, in particular medical or dental, cleaning or care device preferably further comprises at least one of the following elements: a conveying device for conveying a cleaning or care medium; a dispensing device, in particular connected to the conveying device, for dispensing a cleaning or care medium onto and/or into the medical or dental instrument; at least one chamber for accommodating the medical or dental instrument to be cleaned or cared for and/or the carrier element; an adjusting device for setting and/or selecting an operating parameter or an operating program; a controller or a microcontroller for controlling the cleaning or care device, in particular the operation of the cleaning or care device; an evaporator for generating steam serving as cleaning medium.

Preferably, the conveying device of the cleaning or care device comprises at least one of the following components: a pump; a connection to a media source, in particular to a container; a connection to a compressed air line; a valve; a conveying line for conveying the cleaning or care medium, in particular from a media source, for example a container for storing a cleaning or care medium, to an instrument to be cleaned or cared for.

Preferably, the dispensing device for dispensing a cleaning or care medium is configured to deliver the cleaning or care medium to the outside and/or inside of the instrument to be cleaned or cared for.

Preferably, the in particular medical or dental cleaning or care device comprises one of the following devices: a sterilizer; a thermal or chemical disinfection device; a cleaning and/or disinfection device (similar in construction to a dishwasher); a care device for dispensing a maintenance medium, for example a lubricant. The cleaning or care device is thus configured to clean, disinfect, sterilize and/or supply a lubricant to the inside and/or outside of the at least one instrument to be cleaned or cared for.

In accordance with an embodiment, a combination is provided, comprising at least one medical or dental instrument, described in particular above, with a first transmitting and receiving unit and a carrier element described above, wherein the at least one coupling antenna of the carrier element is configured to receive and in turn emit electromagnetic radiation comprising data and/or energy which can be transmitted wirelessly between the first transmitting and receiving unit and a second transmitting and receiving unit, in order to support the wireless transmission of the electromagnetic radiation between the first transmitting and receiving unit and the second transmitting and receiving unit. Preferably, the combination also comprises a cleaning or care device as described above.

According to an embodiment there is provided: the use of a carrier element described above when cleaning or caring for or maintaining at least one medical or dental instrument in a cleaning or care device to support wireless transmission of electromagnetic radiation comprising data and/or energy between a first transmitting and receiving unit arranged on the medical or dental instrument and a second transmitting and receiving unit. The carrier element is used in particular in or with a cleaning or care device described above and/or with a medical or dental instrument with a first transmitting and receiving unit described above.

According to an embodiment, a method is provided for the wireless transmission of electromagnetic radiation comprising data and/or energy between a first transmitting and receiving unit arranged on a medical or dental instrument and a second transmitting and receiving unit. A carrier element is provided for supporting the medical or dental instrument, wherein at least one coupling antenna is provided on the carrier element, which is configured to receive the electromagnetic radiation transmitted wirelessly between the first transmitting and receiving unit and the second transmitting and receiving unit and to emit it again in order to support the wireless transmission of the electromagnetic radiation comprising data and/or energy between the first transmitting and receiving unit and the second transmitting and receiving unit. The carrier element with the medical or dental instrument mounted thereon with the first transmitting and receiving unit is inserted into a, in particular medical or dental, cleaning or care device for cleaning or care of the medical or dental instrument. The electromagnetic radiation comprising data and/or energy is transmitted wirelessly between the first transmitting and receiving unit and the second transmitting and receiving unit via at least one coupling antenna. Preferably, the carrier element comprises a carrier element as described above. Preferably, the process is carried out in or with a cleaning or care device described above.

Preferably the electromagnetic radiation comprising data and/or energy is transmitted from the at least one coupling antenna to the first transmitting and receiving unit and/or the electromagnetic radiation is transmitted from the first transmitting and receiving unit to the at least one coupling antenna.

Preferably, the transmission of the electromagnetic radiation comprising data and/or energy takes place before, during or after the insertion of the carrier element with the medical or dental instrument mounted thereon, which is to be cleaned or cared for, with the first transmitting and receiving unit into the cleaning or care device, in particular into the chamber for receiving the medical or dental instrument to be cleaned or maintained. Preferably, the electromagnetic radiation comprising data and/or energy is transmitted before, during or after closing or locking an opening of the cleaning or care device, through which the carrier element with the medical or dental instrument with the first transmitting and receiving unit to be cleaned or cared for and supported thereon is introduced into the cleaning or care device. The opening is connected in particular to the chamber for receiving the medical or dental instrument to be cleaned or cared for. The opening can be closed or locked in particular by a lid or door. In particular, the lid or door is movably, preferably rotatably or pivotably, attached to the cleaning or care device, for example to the housing. The transmission of electromagnetic radiation comprising data and/or energy is particularly preferably carried out after the cleaning or care of the medical or dental instrument has been completed. Particularly preferably, the transmission of electromagnetic radiation comprising data and/or energy is completed before opening the lid or door for removing the cleaned or cared for instrument. These measures ensure in an advantageous way that electromagnetic radiation, especially data, especially preferably an identification code that can be clearly assigned to an instrument, is only transmitted when the instrument to be cleaned or cared for has been placed in the cleaning or care device or when the cleaning or care has been completed.

Preferably, the at least one medical or dental instrument is fixed to the carrier element by a (mechanical) positioning element, in particular a holder, in particular by a positioning element described above. Particularly preferably, the medical or dental instrument is fixed to the holder or by the positioning element in a determined position in such a way that the first transmitting and receiving unit faces the at least one coupling antenna and/or extends in the direction of the at least one coupling antenna, so that the wireless communication, in particular the transmission of the electromagnetic radiation, between the first transmitting and receiving unit and the at least one coupling antenna is improved in an advantageous manner.

These and other embodiments will be described below with reference to the following drawings.

DETAILED DESCRIPTION

Figure 1:
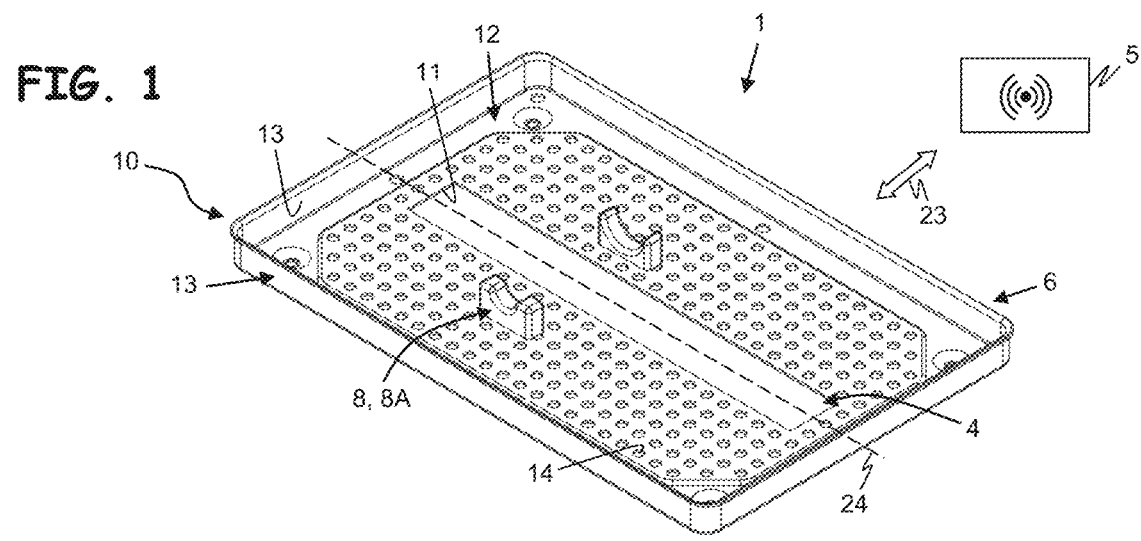
FIG. 1 shows a carrier element for supporting or holding at least one medical or dental instrument in a cleaning or care device in the form of a tray with a slot-shaped coupling antenna arranged in a bottom of the tray.
Figure 2:
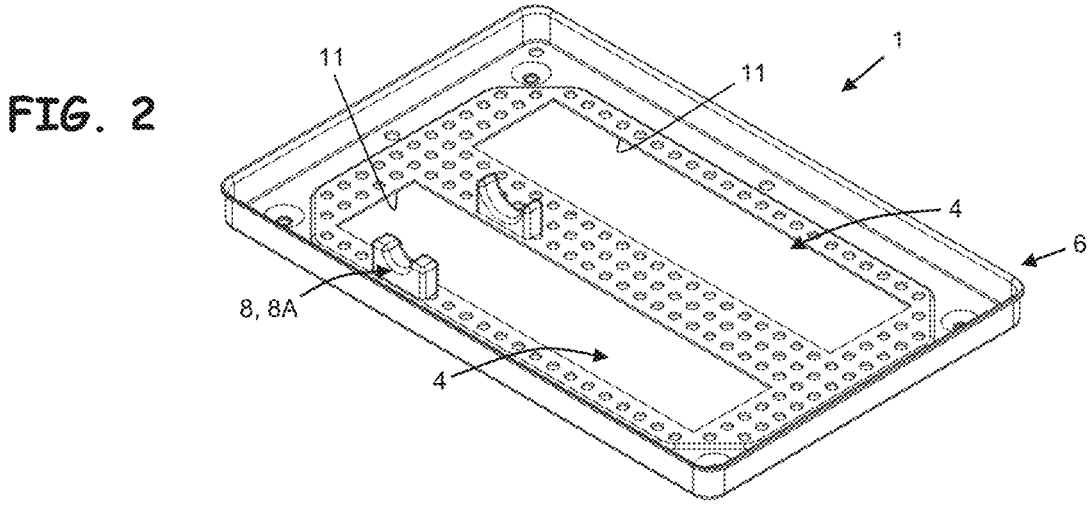
FIG. 2 shows a carrier element in the form of a tray with a plurality of slot-shaped coupling antennas arranged in a bottom of the tray.

FIGS. 1-11 show different carrier elements 1 for supporting or holding at least one medical or dental instrument 2 (see FIGS. 4 and 6) in a cleaning or care device 50 for cleaning or care of the at least one medical or dental instrument 2 in the cleaning or care device 50. The carrier element 1 is provided to be accommodated in the cleaning or care device 50.

FIGS. 1-4 and 9-11 show a carrier element 1 configured as a tray 6. The tray 6 comprises a plurality of outer walls 10, for example a flat and/or plate-shaped base 12 and a plurality of side walls 13 connected to it and surrounding the base plate 12. The base 12 comprises a large number of openings 14 or screen openings which serve as a passage for a cleaning or care product. The openings 14 are preferably round, oval or polygonal, the corners of which are all arranged on a common circumference.

FIGS. 5-8 show a carrier element 1 in the form of a cassette 7. The cassette 7 comprises a plurality of outer walls 10, for example a base 15, a plurality of side walls 16 connected to it and surrounding the base 15, and a lid 17, which is configured to pivot relative to the base 15 and the side walls 16. The base 15, the side walls 16 and the lid 17 delimit an inner space 18 of the cassette 7 from the surroundings. A large number of openings 19, preferably elongated openings, are provided on the base 15 and on the lid 17, which serve as a passage for a cleaning or care product.

At least one positioning element 8, in particular a holder 8A, may be provided on the carrier element 1, 6, 7 in order to position and/or fix the at least one medical or dental instrument 2 on the carrier element 1, 6, 7 (see in particular FIGS. 1, 2, 4, 6 and 9). Alternatively, it is also possible not to provide a positioning element 8 on the carrier element 1, 6, 7 or to remove it from the carrier element 1, 6, 7 (if the positioning element 8 and the carrier element 1, 6, 7 are detachable from each other) so that the at least one medical or dental instrument 2 is accommodated loosely or without a defined position or fastening in the carrier element 1, 6, 7.

For the detachable connection of the at least one positioning element 8, 8A with the carrier element 1, 6, 7, it is in particular provided to insert a connecting element of the positioning element 8, 8A, for example an extension, in one of the openings 14, 19 of the carrier element 1, 6, 7.

The at least one positioning element 8 is configured as a holder 8A with a plug-in receptacle or a clamping element into which the medical or dental instrument 2 to be cleaned or cared for can be inserted. The positioning element 8 is configured in particular such that the medical or dental instrument 2 is disposed in a specific or predefined position, orientation and/or arrangement with respect to the carrier element 1, 6, 7 and/or a coupling antenna 4 of the carrier element 1, 6, 7, so that preferably a transmitting and receiving unit 3 of the instrument 2 faces the at least one coupling antenna 4.

Figures 4, 5, 6:
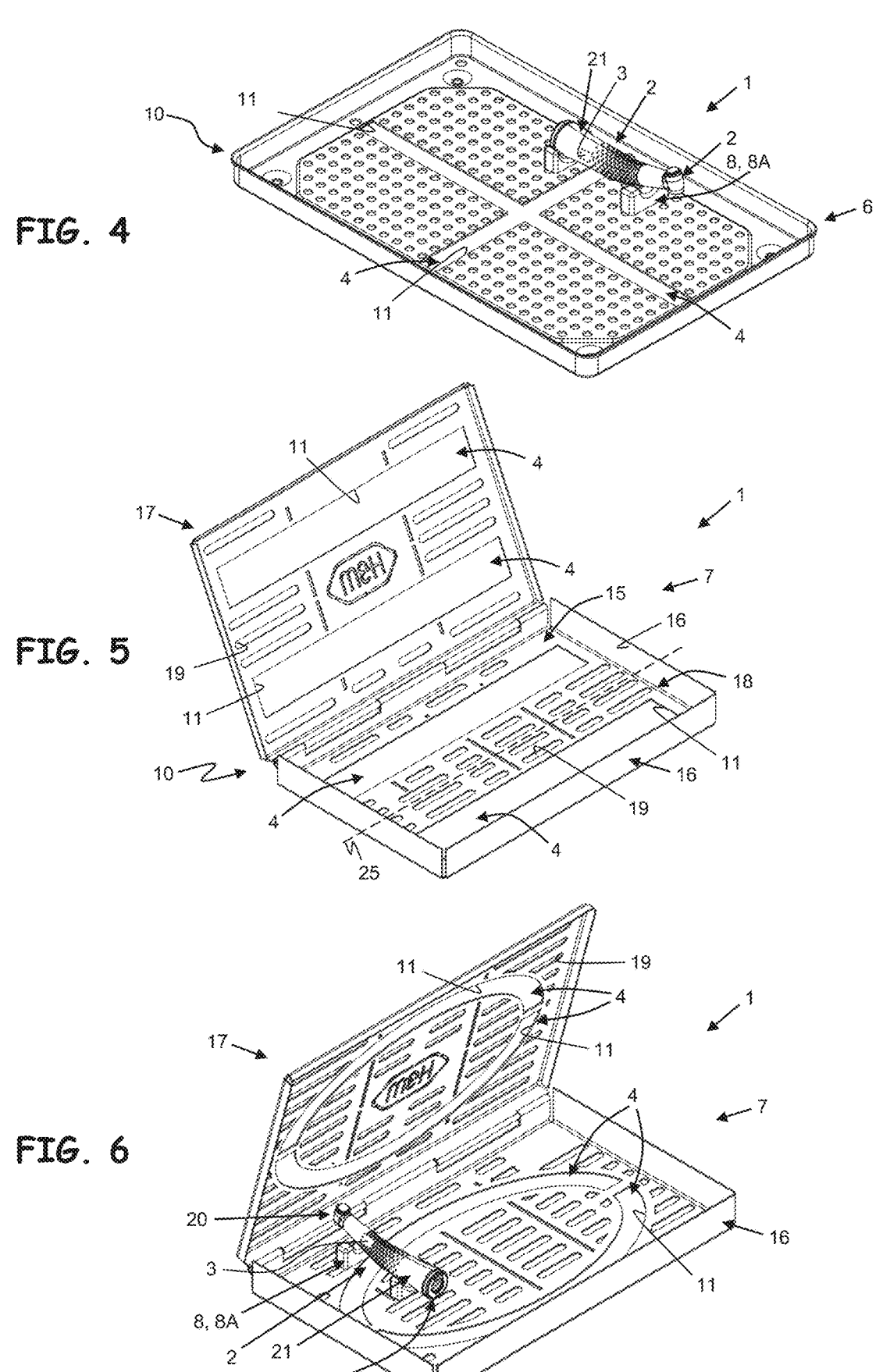
FIG. 4 shows a carrier element in the form of a tray with a plurality of slot-shaped coupling antennas arranged in a bottom of the tray at an angle to each other.
FIG. 5 shows a carrier element for supporting or holding at least one medical or dental instrument in a cleaning or care device in the form of a cassette with a plurality of coupling antennas provided in a bottom and in a cover of the cassette.
FIG. 6 shows a carrier element in the form of a cassette with a plurality of curved coupling antennas provided in a bottom and in a cover of the cassette.
Figure 7:
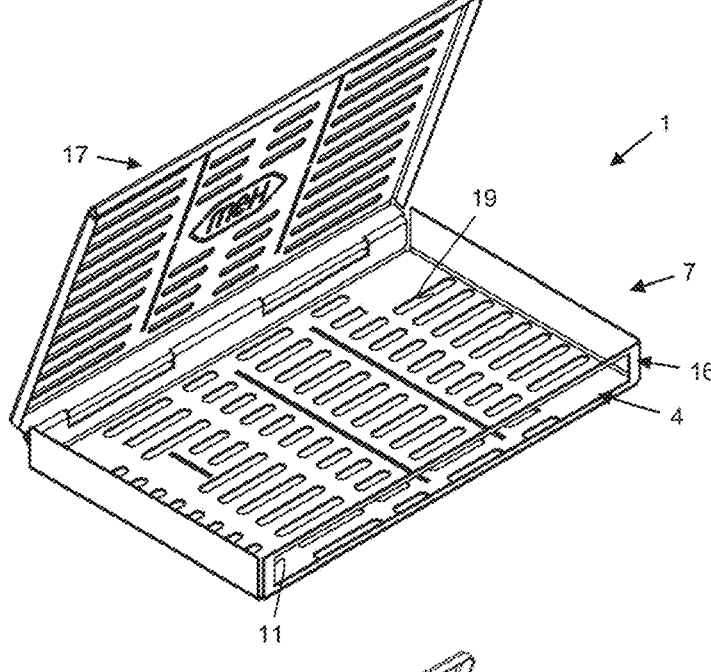
FIG. 7 shows a carrier element in the form of a cassette with a coupling antenna provided in a side wall of the cassette.

FIGS. 4 and 6 show an instrument 2 to be cleaned or cared for or maintained, which is positioned and fixed to the carrier element 1 by a positioning element 8, 8A. The instrument 2 is configured as a dental handpiece or contra-angle handpiece. The handpiece or contra-angle handpiece 2 comprises a head section 20, which has a tool holder for fastening a treatment tool and/or a treatment medium delivery device, and a handle section 21 adjoining the head section 20, and preferably bent along a longitudinal axis. The handle section 21 preferably ends in a coupling 22 for connecting the instrument 2 to a control and/or supply unit for supplying energy and/or a treatment medium.

A first transmitter and receiver unit 3, for example an RFID label, is arranged on the instrument 2 for wireless transmission of data and/or energy comprising electromagnetic radiation, especially in the UHF and/or SHF frequency or wavelength range. The first transmitter and receiver unit 3 can be arranged outside the instrument 2, in particular on its outer sleeve, or inside the instrument 2, in particular in its hollow outer sleeve. The first transmitter and receiver unit 3 can be located in the head section 20 or in the handle section 21, both in that part of the handle section 21 which extends between the head section 20 and the bend, or in that part of the handle section 21 which extends between the bend and the coupling connection 22, or directly in the area of the bend of the handle section 21.

The first transmitting and receiving unit 3 and a second transmitting and receiving unit 5 (see FIG. 1) spaced therefrom are configured to communicate (see numeral 23) with each other in order to establish a wireless transmission of electromagnetic radiation comprising data and/or energy, in particular in the UHF and/or SHF frequency or wavelength range, between the transmitting and receiving units 3, 5. The second transmitting and receiving unit 5 is configured as a reading and/or receiving device, for example. The second transmitter/receiver unit 5 can either be configured as a separate, independent device (see FIG. 1) or as an (integral) part of a device that is operatively and/or communicatively connected to the medical or dental instrument 2, for example the cleaning or care device 50 (see FIG. 12).

Energy transmitted between the first and second transmitting and receiving units 3, 5 comprises in particular energy for operating the first transmitting and receiving unit 3. Data transmitted between the first and second transmitting and receiving units 3, 5 comprise in particular data for identifying the instrument 2, for example a code for identifying the instrument 2, and optionally further data, for example data concerning the cleaning or care status of the instrument 2, the number and/or type of cleaning or care processes which the instrument 2 has already undergone or may still undergo, an operating program or at least one operating parameter which is to be set automatically on the cleaning or care device 50 during the cleaning or care of the instrument 2, and similar data.

The carrier elements 1, 6, 7 of FIGS. 1-9 and 11 have at least one coupling antenna 4 which is configured to receive and in turn emit the electromagnetic radiation transmitted wirelessly between the first and second transmitting and receiving units 3, 5 in order to support or improve the wireless transmission of the electromagnetic radiation comprising data and/or energy between the first and second transmitting and receiving units 3, 5. The at least one coupling antenna 4 affects, for example, the direction of emission of the electromagnetic radiation comprising data and/or energy and/or increases the energy density of the electromagnetic radiation and/or causes a concentration of the electromagnetic radiation.

The at least one coupling antenna 4 can have a variety of different dimensions and/or shapes and/or designs, some of which are shown as examples in FIGS. 1-9 and 11 and described below. All coupling antennas 4 according to any embodiment, which are configured to receive the electromagnetic radiation transmitted wirelessly between the first and second transmitting and receiving units 3, 5 and to emit it again in order to support the wireless transmission of the electromagnetic radiation comprising data and/or energy between the first and second transmitting and receiving units 3, 5, are, however, common in that they are configured, in particular dimensioned and shaped to match the wavelength or frequency of the electromagnetic radiation to be transmitted or transmitted between the first and second transmitting and receiving units 3, 5, in particular electromagnetic radiation in the UHF and/or SHF frequency or wavelength range. Preferably, the coupling antennas 4 are configured in such a way that the transmission of the electromagnetic radiation between the first and second transmitting and receiving units 3, 5 is improved due to the effect of the coupling antennas 4 compared to a transmission of the electromagnetic radiation without the coupling antennas 4. For example, due to the effect of the coupling antennas 4 during the wireless transmission (and in comparison with the transmission of the electromagnetic radiation without the coupling antenna 4), at least one of the following effects is achievable: a reduced influence of interference variables on the electromagnetic radiation or its transmission; a lower loss of data and/or transmitted energy transmitted by the electromagnetic radiation; a lower noise in the transmitted data; a (per time unit) higher amount of transmitted energy and/or data; a (per time unit) faster transmission of a certain amount of energy and/or data.

Figure 8:
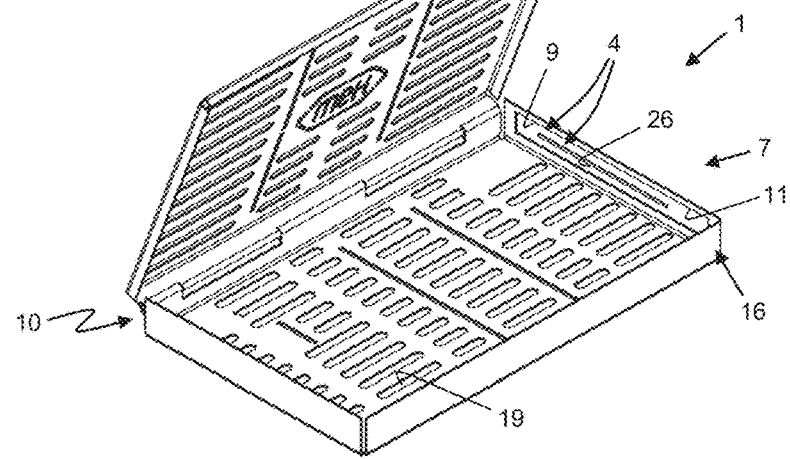
FIG. 8 shows a carrier element in the form of a cassette with a slot-shaped coupling antenna in a side wall of the cassette, in which a linear coupling antenna is accommodated.
Figure 9:
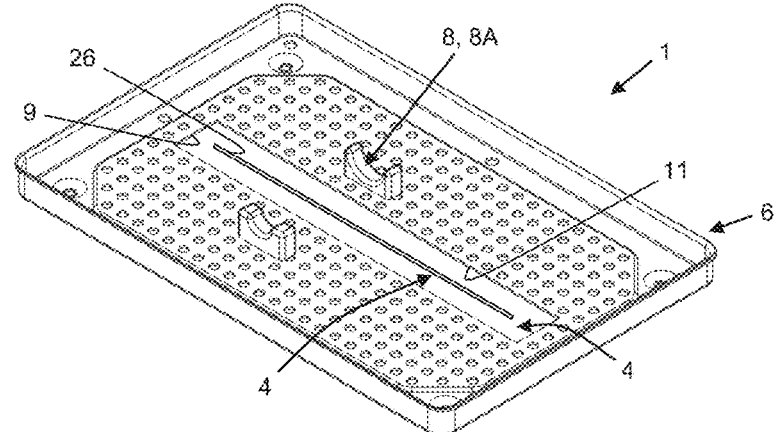
FIG. 9 shows a carrier element in the form of a tray with a slot-shaped coupling antenna provided in a bottom of the tray, in which a linear coupling antenna is accommodated.

The coupling antennas 4 shown in FIGS. 1-9 and 11 comprise either only at least one flat top antenna (see FIGS. 1-7) or only at least one (geometrically) linear antenna, the electrical conductor 26 of which comprises in particular a metallic wire or rod (see FIG. 11), or at least one flat top antenna and one linear antenna, the electrical conductor 26 of which comprises in particular a metallic wire or rod (see FIGS. 8, 9).

The trays 6 shown in FIGS. 1-4, 9 comprise one or more coupling antennas 4 formed as flat top antennas. The flat top antennas are formed as elongated slots 11 in an outer wall 10, i.e., in the base 12, of the carrier element 1, 6. At least the bottom 12 of the tray 6, preferably the entire tray 6, is made of metal, which additionally improves the wireless transmission of electromagnetic radiation comprising data and/or energy.

The cassettes 7 shown in FIGS. 5-8 comprise one or more coupling antennas 4. The coupling antennas 4 are formed as elongated slots 11 in an outer wall 10, i.e., in the bottom 15 and/or in the lid 17 and/or in a side wall 16 (long side or narrow side), of the carrier element 1, 7. At least that outer wall 10 of the cassette 7 in which a flat top antenna is provided, preferably the entire cassette 7, is made of metal, so that the wireless transmission of electromagnetic radiation comprising data and/or energy is additionally improved.

The positioning elements 8, 8A are preferably arranged on the tray 6 or on the cassette 7 in such a way that a medical or dental instrument 2 positioned therein projects over a flat top antenna or a slot 11 and in particular the first transmitter and receiver unit 3 is located near or above the flat top antenna or slot 11 (see in particular FIGS. 4 and 6; such an arrangement of the positioning elements 8, 8A is also possible for FIGS. 1-3, 5, 9). This further improves the wireless transmission of electromagnetic radiation comprising data and/or energy.

The slot 11 is formed as a passage or opening passing through the outer wall 10 (12; 15-17) and in particular does not comprise any solid body. Alternatively, the slot 11 may be filled with an electrically non-conductive material, for example plastic or glass or ceramic, to form a continuous outer wall 10, in particular a continuous bottom 12, 15, to prevent the instrument 2 to be cleaned or cared for from falling through the slot 11 and possibly being lost. The electrically non-conductive material is, for example, in the form of a continuous plate or a plate with holes which partially or completely fills slot 11.

Figure 3:
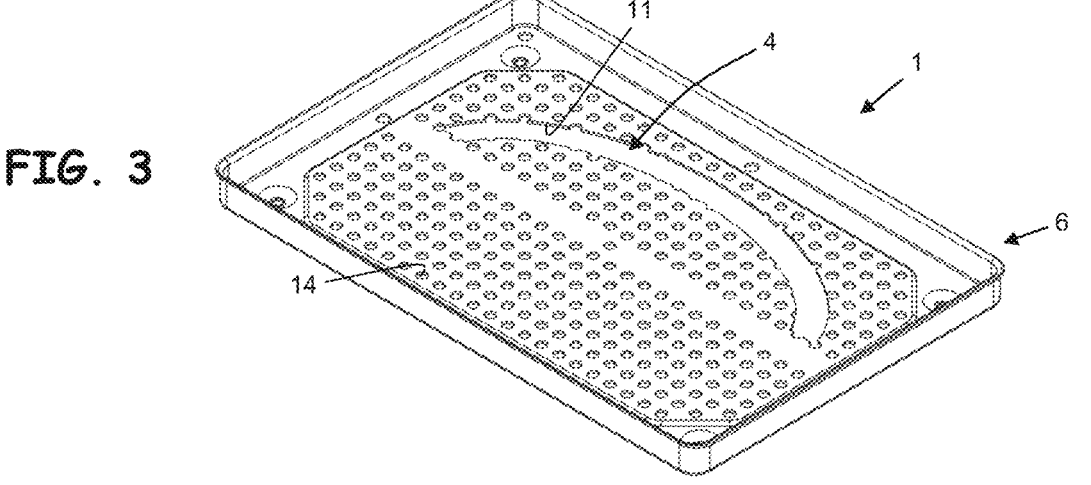
FIG. 3 shows a carrier element in the form of a tray with a slot-shaped, curved coupling antenna arranged in a bottom of the tray.

The slots 11 in FIGS. 1, 2, 4, 5 and 7-9 are straight and/or essentially rectangular. The slots 11 of FIGS. 3 and 6 are curved, allowing the slot 11 to be longer than the long side of the tray 6 or cassette 7, for example to have the appropriate length for the wavelength of electromagnetic radiation to be transmitted. A curved slot 11 can have a variety of other shapes in addition to the circular arc shape shown in FIGS. 3, 6, for example S-shaped, spiral or similar shapes.

The slot 11 or at least one of the slots 11 of the flat top antennas may be arranged differently with respect to a longitudinal axis 24 of the tray 6 or with respect to a longitudinal axis 25 of the cassette 7 and may have one or more of the following arrangements: central in the carrier element 1, 6, 7 so that in particular the longitudinal axis 24, 25 also forms the central axis of slot 11 (see FIGS. 1 and 4—long slot, 9); off-centre (see FIGS. 2, 3, 4—short slot, 5-8) and preferably parallel to the longitudinal axis 24 (see FIGS. 2, 5-8), in particular when there are a plurality of slots 11; angled, for example orthogonal, to the longitudinal axis 24 (see FIGS. 3 and 4—short slot, 6). The different arrangement and shape of slots 11 can be used to create carrier elements 1, 6, 7, which are advantageously adapted to certain instruments 2, for example to the length of instrument 2 and/or to the position of the first transmitter and receiver unit 3 on instrument 2.

Figure 11:
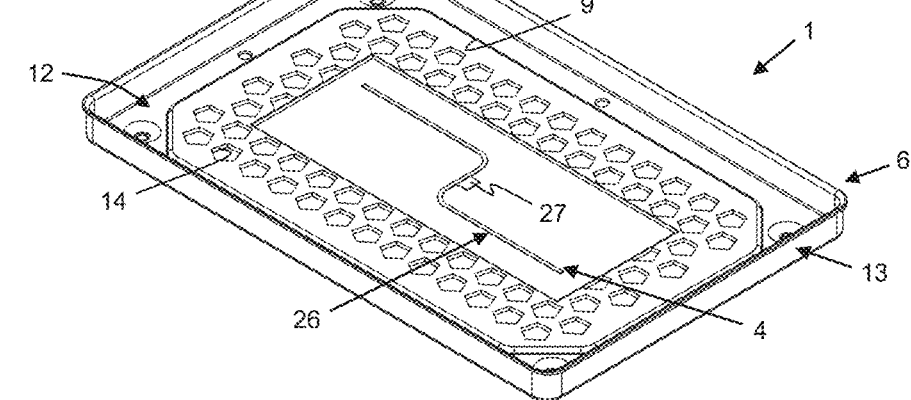
FIG. 11 shows a carrier element in the form of a tray with a base plate of electrically non-conductive material inserted into the tray, in which a linear coupling antenna is accommodated.

The carrier elements 1, 6, 7 of FIGS. 1, 3, 7, 11 have a single coupling antenna 4 which is either a flat top antenna, in particular with a slot 11 (see FIGS. 1, 3, 7), or a metallic linear antenna with a rod or wire-shaped electrical conductor 26 (see FIG. 11).

The carrier elements 1, 6, 7 of FIGS. 2, 4-6, 8, 9 comprise a plurality of coupling antennas 4, which are either only configured as slot-shaped flat top antennas 11 (see FIGS. 2, 4-6) or have at least one slot-shaped flat top antenna 11 and at least one metallic linear antenna with a rod-shaped or wire-shaped electrical conductor 26 (see FIGS. 8-9). Of course, it is also possible to produce a carrier element 1, 6, 7 with exclusively a plurality of metallic, linear antennas, each with a rod-shaped or wire-shaped electrical conductor 26. As can be seen from the Figures, the multiple coupling antennas 4 can either all be provided on a single and/or common outer wall 10, especially on the base 12, 15 or a side wall 16 (see FIGS. 2, 4, 8, 9), or on different outer walls 10, especially on the base 12, 15 and the cover 17 (see FIGS. 5, 6).

In FIGS. 8, 9, the metallic linear antenna is located in a recess 9, this recess 9 being formed by the slot 11 of the flat top antenna, which is advantageous to facilitate the manufacture of the carrier element 1 with the two coupling antennas 4. The slot 11 is at least partially filled with an electrically non-conductive material (as described above) in which the metallic linear antenna is accommodated or embedded. However, it is of course also possible to arrange the flat top antenna formed by the slot 11 and the metallic linear antenna at a distance from each other, either on the same outer wall 10 or on different outer walls 10. If the two coupling antennas 4 are arranged separately and at a distance from each other, the metallic linear antenna is thus arranged in its own separate receptacle 9.

If a plurality of coupling antennas 4 of the same type, i.e., exclusively flat top antennas or exclusively metallic linear antennas, are present on a carrier element 1, the a plurality of coupling antennas 4 of the same type may be identical (see FIGS. 2, 5, 6) or they may differ in at least one parameter or property, for example with respect to their shape and dimensions (see FIG. 4). The two slot antennas 11 of tray 6 of FIG. 4 differ, for example, in their length. Similar coupling antennas 4 with at least one different property can of course also be provided in the same way on a cassette 7.

The provision of a plurality of coupling antennas 4 on a carrier element 1 offers a plurality of advantages: for example, different frequencies or wavelengths of electromagnetic radiation can be transmitted if the coupling antennas 4 have different lengths (see FIGS. 4, 8, 9) and/or exact positioning of at least one instrument 2 relative to the coupling antennas 4 is less critical, since the multiple coupling antennas 4 ensure that the first transmitting and receiving unit 3 of instrument 2 is at least sufficiently close to one of the multiple coupling antennas 4 (see FIGS. 4-6).

The provision of at least one slot antenna 11 in a side wall 16 (see FIGS. 7, 8) reduces the risk of the at least one instrument 2 falling unintentionally through a slot 11 compared to the arrangement of the slot 11 in the base 12, 15. The arrangement of a slot antenna 11 in a side wall 13 is conceivable in a corresponding manner for a tray 6.

FIG. 11 shows a tray 6 with a metallic, linear antenna arranged in a recess 9. In contrast to the embodiment in FIGS. 8 and 9, however, the recess 9 in FIG. 11 is not dimensioned in such a way that it acts as a coupling antenna 4 or as a flat top antenna, in particular not as a coupling antenna 4 for electromagnetic radiation in the UHF and/or SHF frequency or wavelength range. The wireless transmission, i.e., the reception and emission of electromagnetic radiation comprising data and/or energy, is thus exclusively effected by the metallic linear antenna according to the embodiment in FIG. 11.

The recess 9 is in turn at least partially filled with an electrically non-conductive material (as already described above), in which the metallic linear antenna is accommodated or embedded. The tray 6, especially the bottom 12 and the side walls 13, can be made of metal, plastic, glass or ceramic.

The coupling antenna 4, configured in FIG. 11 as a (geometrically) linear antenna, comprises an electrical conductor 26, in particular in the form of a metallic wire or rod. The (geometrically) linear antenna is configured in particular as a rod antenna or as a wire antenna or as a dipole antenna. Preferably an electrical component 27 is connected to the electrical conductor 26. The electrical component 27 comprises, for example, a signal amplifier to support the transmission of the electromagnetic radiation comprising data and/or energy and/or a memory element, which in particular stores an identification code of carrier element 1 or a code for identification of carrier element 1 via an external database.

The embodiment shown in FIG. 11 and described above can be transferred to a cassette 7 in a corresponding manner.

Figure 10:
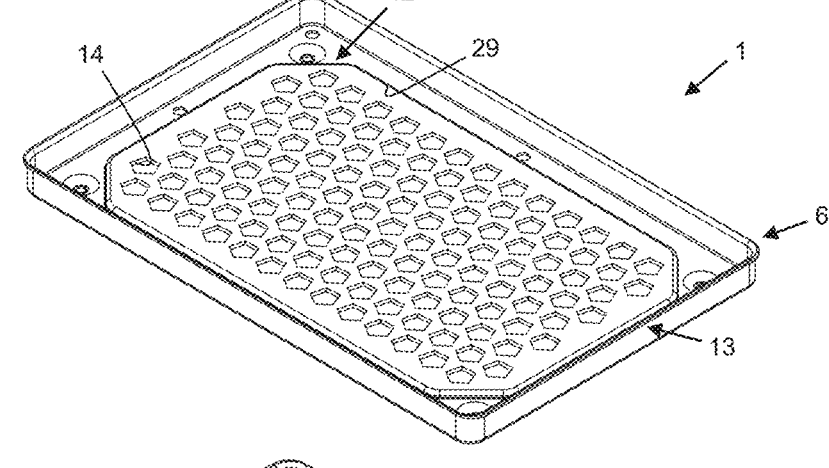
FIG. 10 shows a carrier element in the form of a tray with a base plate of electrically non-conductive material inserted into the tray.

The tray 6 shown in FIG. 10 does not have a coupling antenna 4, in particular a coupling antenna 4 for electromagnetic radiation in the UHF and/or SHF frequency or wavelength range. The tray 6 is preferably intended for use with a carrier element 1, 6, 7 described above with a coupling antenna 4, in particular for joint use in a cleaning or care appliance 50, wherein the tray 6 is configured in such a way that it interferes (negatively) as little as possible a wireless transmission of electromagnetic radiation comprising data and/or energy, preferably in the UHF and/or SHF frequency or wavelength range, in particular between a first transmitting and receiving unit 3 and a second transmitting and receiving unit 5, particularly preferably with the aid of a coupling antenna 4.

For this purpose, at least a part of floor 12, preferably the entire floor 12 is made of an electrically non-conductive material, for example plastic or glass or ceramic. Preferably, the electrically non-conductive material is formed as a plate, which is inserted in particular in a recess 29 of the tray 6. The recess 29 is formed, for example, by the side walls 13 and/or parts of the bottom 12. The side walls 13 and/or parts of the bottom 12 can be made of metal or alternatively of one of the mentioned electrically non-conductive materials.

Figure 12:
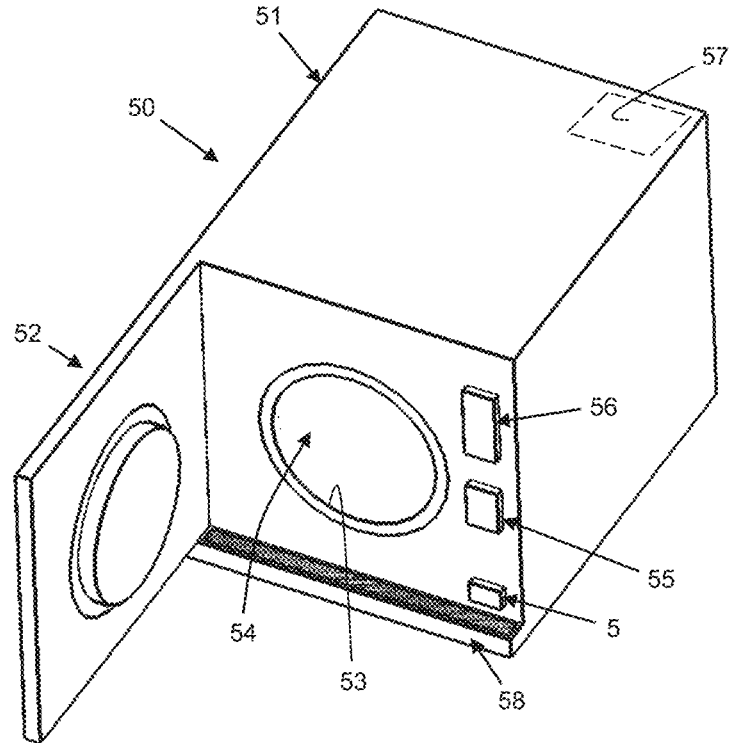
FIG. 12 shows an embodiment of a cleaning or care device for at least one medical or dental instrument for use with a carrier element with at least one coupling antenna.

The cleaning or care device 50 shown in FIG. 12 for at least one medical or dental instrument 2 is configured as a sterilizer, in particular a steam sterilizer. The cleaning or care device 50 is intended for use with a carrier element 1 with at least one coupling antenna 4 and/or the tray of FIG. 10.

The sterilizer 50 comprises an outer housing 51 with a plurality of walls and a cover 52 which is movable relative to the walls. An opening 53 is provided on one of the walls of the housing 51, which is connected to a cleaning or care room 54 of the sterilizer 50. Through this opening 53 an instrument 2 to be cleaned or maintained and a carrier element 1, 6, 7 can be inserted into or removed from the cleaning or care room 5.

One or more operating elements 55 are provided on the housing 51, which are used, for example, to select different operating programs or to set operating parameters. A display 56 shows the selected operating programs or operating parameters or other data or characteristic values relevant to the operation of the sterilizer 50.

Inside the housing 51, in addition to the cleaning or care room 54 configured as a pressure vessel, a supply device for introducing at least one cleaning or care medium, in particular steam, into the cleaning or care room 54 and a control device 57 are provided. The cleaning or care room 5 is configured to accommodate the at least one carrier element 1. As already described above, it is also possible that the second transmitting and receiving unit 5, in particular a reader, is arranged on the sterilizer 50, in particular on the housing 51 or inside the housing 51.

The control device 57 is configured to control and/or regulate the operation of the cleaning or care unit 50, in particular the course of the cleaning and/or care procedures and the keeping of the parameters during the cleaning and/or care procedures. The second transmitting and receiving unit 5 is either configured as an integral part of the control device 57 and/or is at least communicatively connected to the control device 57. The one or more antennas of the second transmitting and receiving unit 5 are arranged on the outer housing 51, for example on one of the walls of the outer housing 51, in particular at least one antenna is arranged on the wall with the opening 53, and/or on the cover 52 and/or on a projection 58 projecting over a wall of the outer housing 51, in particular that wall with the opening 53.

The second transmitting and receiving unit 5, in particular the reader, are configured to communicate with the first transmitting and receiving unit 3, in particular the RFID label, to transmit energy to the first transmitting and receiving unit 3, if necessary, via the coupling antenna 4 of the carrier element 1, and to interrogate the data stored on the first transmitting and receiving unit 3 wirelessly via the coupling antenna 4 of the carrier element 1. The second transmitting and receiving unit 5 can preferably have further, in particular electrical, components, for example a signal amplifier for the transmissible data, a signal processing unit, an energy source or a connection to an energy source. Alternatively, one or more of these elements are part of the control device 57.

Preferably the control device 57 is configured to receive the data read out from the first transmitting and receiving unit 3 by the second transmitting and receiving unit 5 and, based on these data, to identify the at least one medical or dental instrument 2 located on the carrier element 1. Furthermore, the control device 57 can also be configured to operate the cleaning or care device 50 on the basis of the received data, in particular to select a cleaning or care method or to set parameters for the operation of the cleaning or care device 50 automatically.

The control device 57 is preferably configured to transmit data about a cleaning or care method performed by the cleaning or care device 50 to the second transmitting and receiving unit 5, so that the second transmitting and receiving unit 5 transmits these data via the coupling antenna 4 to the first transmitting and receiving unit 3, in particular to the RFID label of the instrument 2. Data transmitted to the first transmitting and receiving unit 3 comprises, in particular, information on whether instrument 2 has been cleaned or maintained, the method used to clean or maintain it, the parameters (temperature, pressure, etc.) for which it has been cleaned or maintained, or the total number of times it has been cleaned or maintained.

The described or depicted embodiments serve in particular to illustrate the invention. The features disclosed in an embodiment are therefore not limited to this embodiment but can be combined individually or together with one or more features of one of the other embodiments. In particular, the type, number, shape and position of the coupling antennas shown in the individual embodiments are exemplary and can be transferred between the embodiments.

What is claimed is:

1. A carrier element for supporting at least one medical or dental instrument in a cleaning or care device for cleaning or caring for the at least one medical or dental instrument, the carrier element comprising:

a passive data and/or energy transmission unit having at least one coupling antenna provided on the carrier element and configured to receive electromagnetic radiation comprising data and/or energy transmitted wirelessly between a first transmitting and receiving unit arranged on the medical or dental instrument and a second transmitting and receiving unit remote from the first transmitting and receiving unit, and wherein the at least one coupling antenna is configured to emit the received electromagnetic radiation again in order to support the wireless transmission of the electromagnetic radiation comprising data and/or energy between the first transmitting and receiving unit and the second transmitting and receiving unit, wherein the at least one coupling antenna is formed by an opening in a wall of the carrier element, wherein the opening is a slot to form a slot antenna, wherein the at least one coupling antenna is a first coupling antenna and wherein the passive data and/or energy transmission unit of the carrier element comprises at least one second coupling antenna, wherein the first coupling antenna and the second coupling antenna are configured to transmit electromagnetic radiation of different frequencies.

2. The carrier element according to claim 1, wherein the carrier element comprises one of: a carrier plate, a tray, a basket or a cassette.

3. The carrier element according to claim 1, wherein at least one positioning element is provided on the carrier element in order to position the at least one medical or dental instrument on the carrier element.

4. The carrier element according to claim 1, wherein the first coupling antenna comprises one of a straight or curved shape.

5. The carrier element according to claim 1, wherein the first coupling antenna is arranged in a first wall of the carrier element and the second coupling antenna is arranged in a second wall of the carrier element, wherein the first wall and the second wall are different walls of the carrier element.

6. The carrier element according to claim 1, wherein the first coupling antenna and the second coupling antenna are arranged in a single shared wall of the carrier element.

7. The carrier element according to claim 1, wherein the second coupling antenna comprises a slot antenna in an outer wall of the carrier element.

8. The carrier element according to claim 1, wherein the first coupling antenna is surrounded by a metallic component of the carrier element or by a metallic portion of the wall of the carrier element.

9. A carrier element for supporting at least one medical or dental instrument in a cleaning or care device for cleaning or caring for the at least one medical or dental instrument, the carrier element comprising:

a passive data and/or energy transmission unit having at least one coupling antenna provided on the carrier element and configured to receive electromagnetic radiation comprising data and/or energy transmitted wirelessly between a first transmitting and receiving unit arranged on the medical or dental instrument and a second transmitting and receiving unit remote from the first transmitting and receiving unit, and wherein the at least one coupling antenna is configured to emit the received electromagnetic radiation again in order to support the wireless transmission of the electromagnetic radiation comprising data and/or energy between the first transmitting and receiving unit and the second transmitting and receiving unit, wherein the at least one coupling antenna is formed by an opening in a wall of the carrier element, wherein the opening is a slot to form a slot antenna, wherein the at least one coupling antenna is a first coupling antenna and wherein the passive data and/or energy transmission unit of the carrier element comprises at least one additional coupling antenna, wherein the at least one additional coupling antenna comprises a linear antenna, wherein the linear antenna is disposed in the opening which forms the first coupling antenna.

10. The carrier element according to claim 9, wherein the first coupling antenna and the at least one additional coupling antenna are configured to transmit electromagnetic radiation of different frequencies.

11. The carrier element according to claim 9, wherein the opening is filled with an electrically non-conducting material.

12. The carrier element according to claim 9, wherein the first coupling antenna is surrounded by a metallic component of the carrier element or by a metallic portion of the wall of the carrier element.

13. The carrier element according to claim 9, wherein the linear antenna comprises one of a rod antenna, a wire antenna and a dipole antenna.

14. The carrier element according to claim 9, wherein the first coupling antenna comprises one of a straight or curved shape.

15. A carrier element for supporting at least one medical or dental instrument in a cleaning or care device for cleaning or caring for the at least one medical or dental instrument, the carrier element comprising:

a plurality of coupling antennas provided on the carrier element and configured to receive electromagnetic radiation comprising data and/or energy transmitted wirelessly between a first transmitting and receiving unit arranged on the medical or dental instrument and a second transmitting and receiving unit, and wherein the plurality of coupling antennas is configured to emit the received electromagnetic radiation again in order to support the wireless transmission of the electromagnetic radiation comprising data and/or energy between the first transmitting and receiving unit and the second transmitting and receiving unit, wherein the plurality of coupling antennas comprises a first coupling antenna and a second coupling antenna, which are different coupling antennas, wherein the first coupling antenna comprises a slot antenna formed in a first wall of the carrier element and a second coupling antenna comprises a slot antenna formed in a second wall of the carrier element, wherein the first wall and the second wall are different walls of the carrier element that are parallel to one another or that are arranged at an angle to one another with the angle not equal to 0°.

16. The carrier element according to claim 15, wherein the carrier element comprises a cassette and the first wall comprises a bottom wall of the cassette and the second wall comprises a lid of the cassette which is configured to pivot relative to the bottom wall.

17. The carrier element according to claim 15, wherein the carrier element comprises a bottom wall and a plurality of side walls that connect to the bottom wall and surrounding the bottom wall, wherein one of the first and second wall comprises one of the side walls of the carrier element.

18. The carrier element according to claim 15, wherein the first coupling antenna and the second coupling antenna differ from one another with respect to at least one of their shape and dimension.

19. The carrier element according to claim 15, wherein the plurality of coupling antennas comprises at least three coupling antennas.

20. The carrier element according to claim 15, wherein at least one of the first and the second coupling antenna is filled with an electrically non-conducting material.

* * * * *